US00PP31807P3

(12) United States Plant Patent
Suphachadiwong

(10) Patent No.: US PP31,807 P3
(45) Date of Patent: May 26, 2020

(54) *VANDA* PLANT NAMED 'SPCDW1806'

(50) Latin Name: *Vanda* spp.
Varietal Denomination: SPCDW1806

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 16/501,451

(22) Filed: Apr. 17, 2019

(65) Prior Publication Data

US 2019/0320571 P1 Oct. 17, 2019

(30) Foreign Application Priority Data

Apr. 17, 2018 (QZ) ..... PBR 2018/1075

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

A new and distinct *Vanda* plant named 'SPCDW1806' which is characterized by a compact growth habit and a freely flowering bloom habit, a very light purple dorsal sepal and very light purple lateral petals which are heavily dotted and reticulated with a mixture of dark red-purple and greyed-purple, very light greyed-orange lateral sepals which are margined red-purple and conspicuously reticulated dark greyed-purple, a labellum with a dark red-purple central lobe and dark red-purple lateral lobes which are radially striped with yellow-white, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1806'.

CROSS REFERENCE TO RELATED APPLICATIONS

This application claims priority to the Community Plant Variety Rights application number 2018/1075, filed Apr. 17, 2018, which is herein incorporated by reference.

BACKGROUND OF THE INVENTION

Parentage: The new *Vanda* plant, 'SPCDW1806', is the result of a planned breeding program. 'SPCDW1806' originated as a seedling from the controlled pollination of *Vanda* 'M38BP5' (not patented), the seed parent, with *Vanda* 'M81R1' (not patented), the pollen parent. Both parents were developed by, and are owned by, the inventor and were never commercially released. The crossing was made by the inventor in his research greenhouse in Bangphra, Thailand in October of 1996.

The new variety was first selected in March of 2001, in a research greenhouse in Bangphra, Thailand belonging to the inventor. After identifying the new variety as a potentially interesting selection, the inventor continued confidential testing and propagation of 'SPCDW1806', assessing stability of the unique characteristics of this variety.

Asexual Reproduction: Asexual reproduction of the new cultivar 'SPCDW1806', by way of mericloning, was first initiated in February of 2012 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1806' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1806'. These characteristics in combination distinguish 'SPCDW1806' as a new and distinct *Vanda* cultivar:

1. *Vanda* 'SPCDW1806' exhibits a compact growth habit and a freely flowering bloom habit; and
2. *Vanda* 'SPCDW1806' exhibits a very light purple dorsal sepal and very light purple lateral petals, which are heavily dotted and reticulated with a mixture of dark red-purple and greyed-purple; and
3. *Vanda* 'SPCDW1806' exhibits very light greyed-orange lateral sepals which are margined red-purple and conspicuously reticulated dark greyed-purple; and 4. *Vanda* 'SPCDW1806' exhibits a labellum with a dark red-purple central lobe, and dark red-purple lateral lobes which are radially striped with yellow-white.

BOTANICAL DESCRIPTION OF THE PLANT

Figure 1:
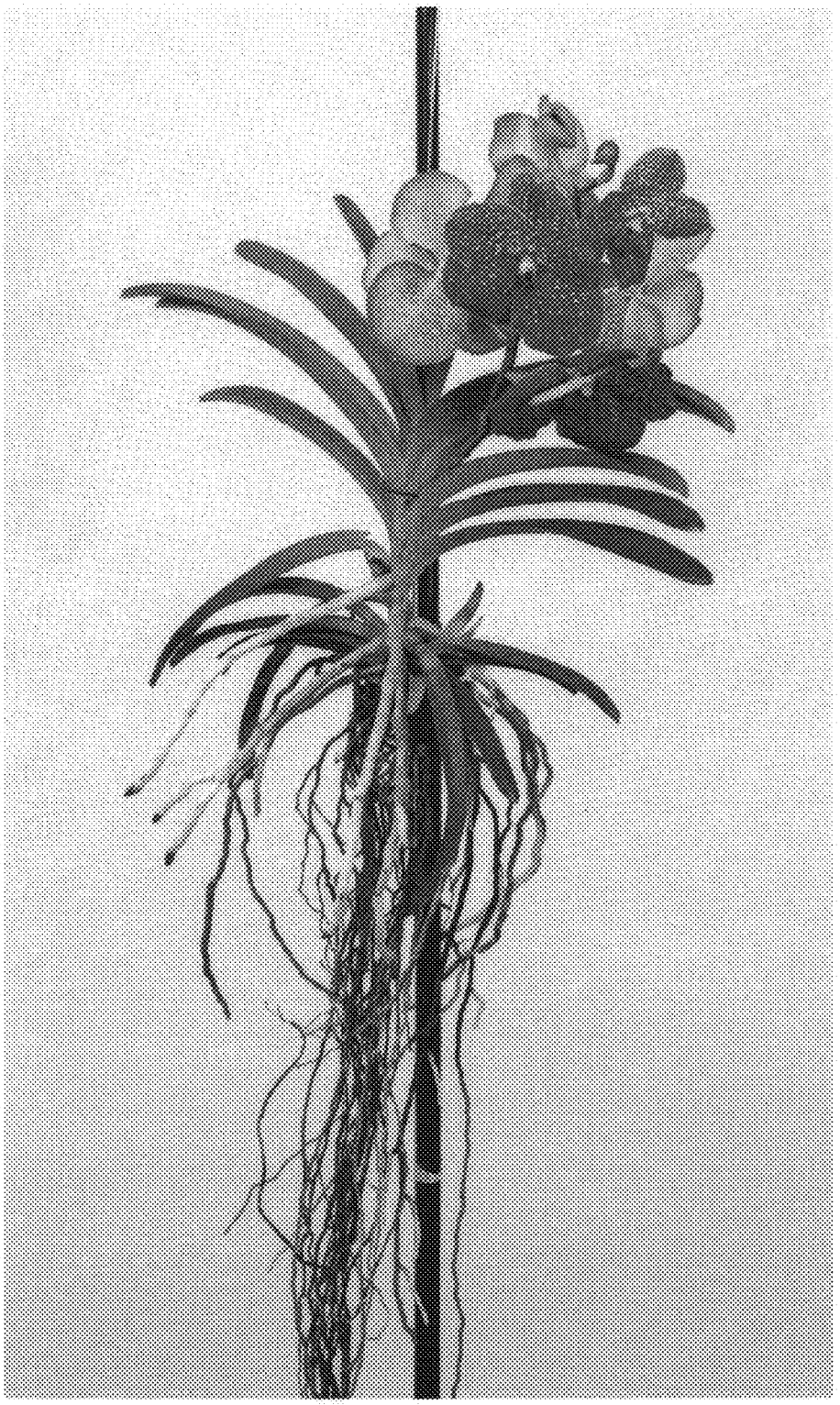
FIG. 1 illustrates, as nearly true as it is reasonably possible to make the same in color photographs of this type, an exemplary plant of 'SPCDW1806' grown in a commercial greenhouse in Honselersdijk, the Netherlands. This plant is approximately 6 years old from the time of mericloning, shown planted in an 8 by 2 cm container.
Figure 2:
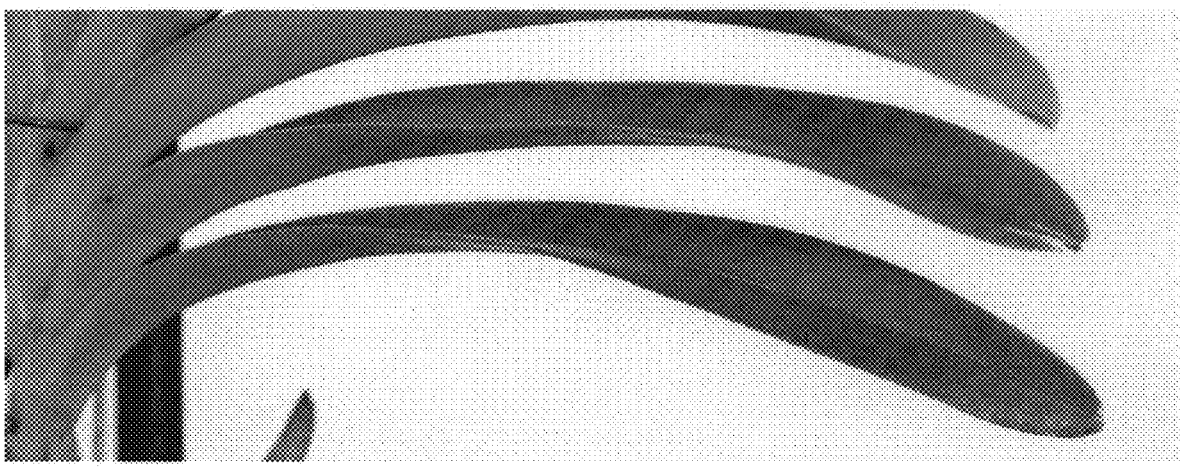
FIG. 2 illustrates, as nearly true as it is reasonably possible to make the same in color photographs of this type, the typical foliage of 'SPCDW1806'.
Figure 3:
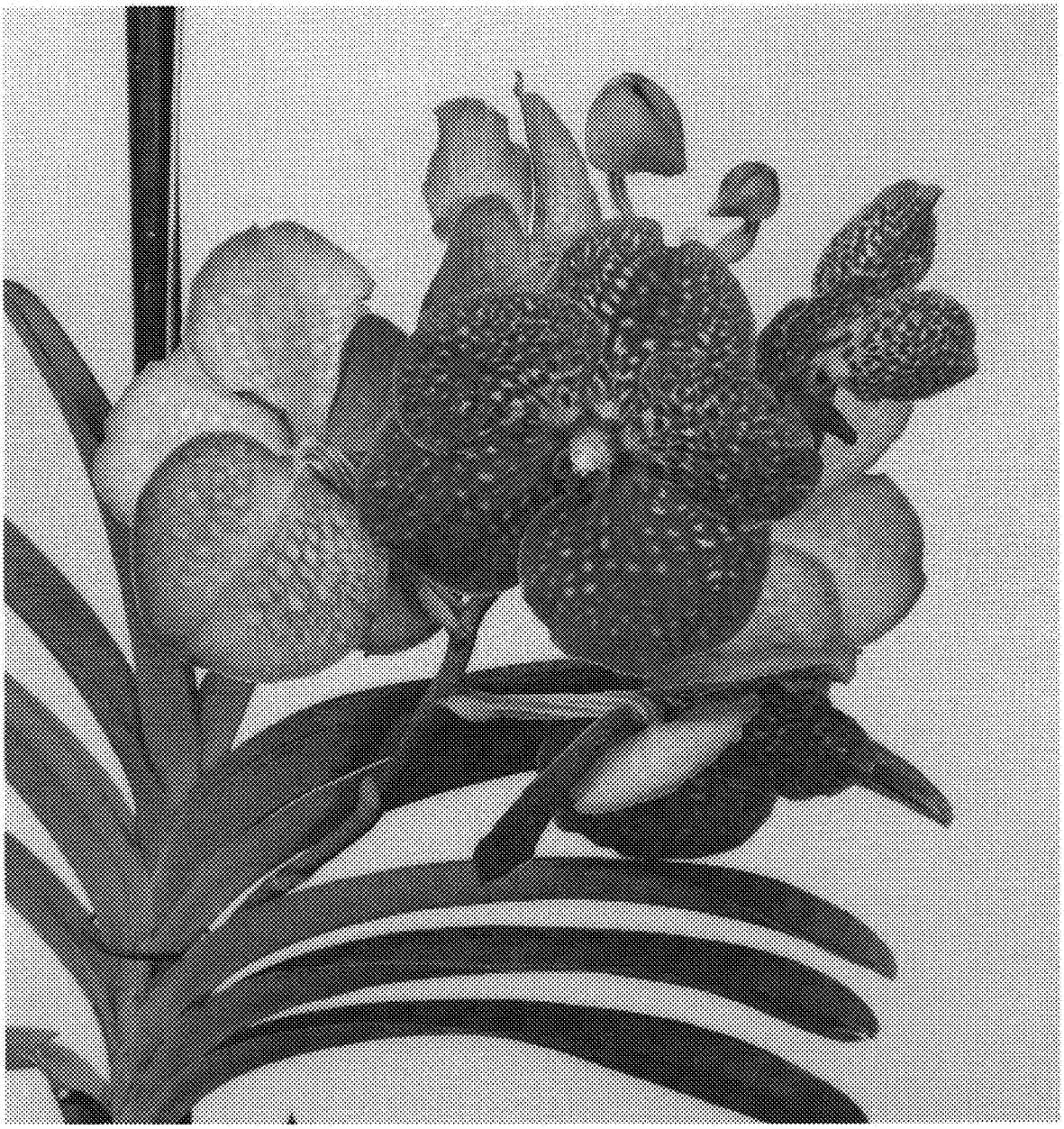
FIG. 3 illustrates, as nearly true as it is reasonably possible to make the same in color photographs of this type, the typical inflorescence of 'SPCDW1806'.
Figure 4:
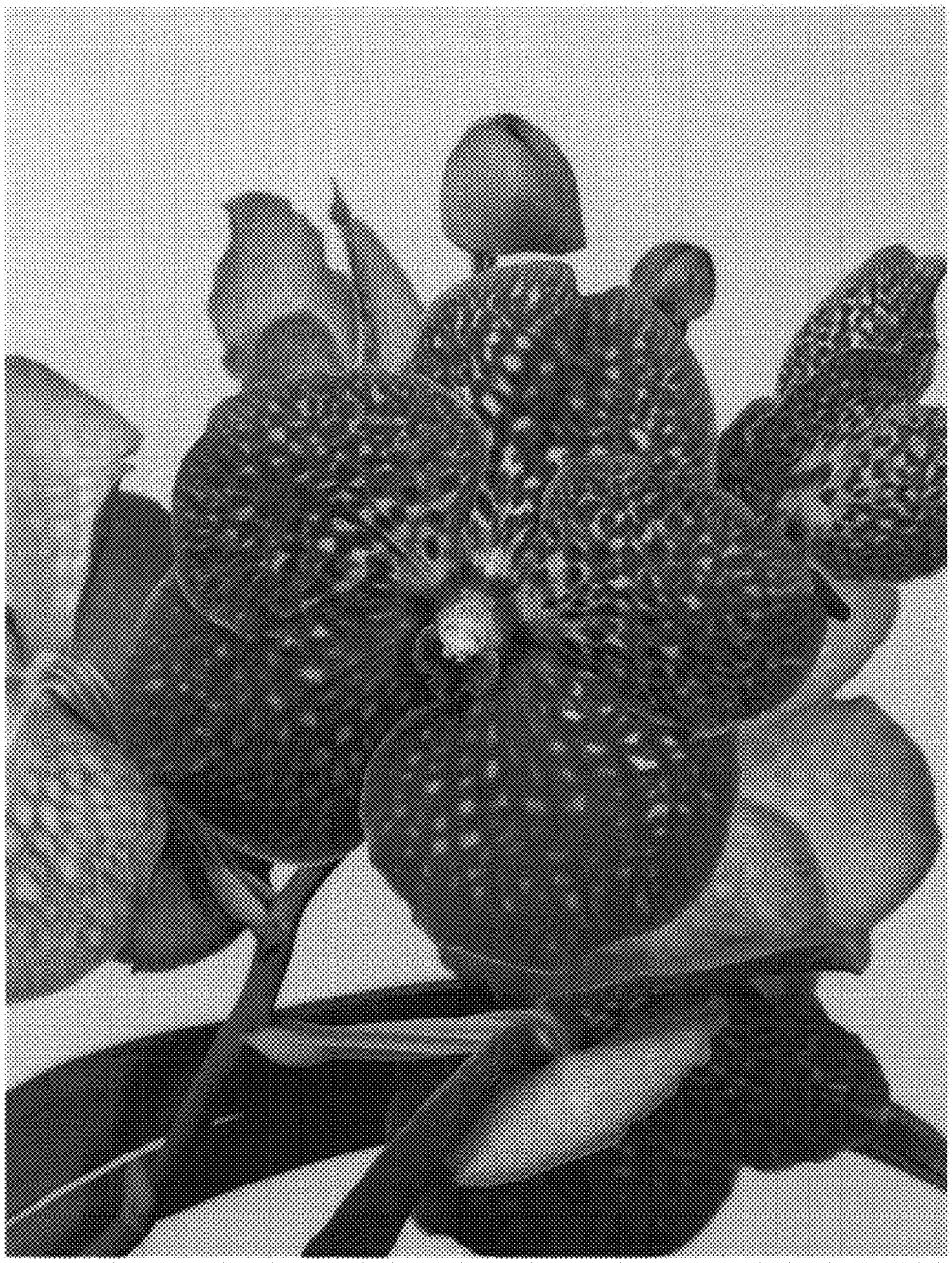
FIG. 4 illustrates, as nearly true as it is reasonably possible to make the same in color photographs of this type, the typical flower of 'SPCDW1806'.

The following observations and measurements made in March of 2019 describe averages from a sample set of six specimens of six year-old 'SPCDW1806' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1806' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1806' and comparisons with the parents and most similar commercial variety of *Vanda* are provided below.

Plant description:

*Growth habit.*—Perennial; monopodial, upright. Single monopodial leafy stem, with flowers carried at or slightly above the leaf plane; inflorescences growing from the leaf axils.

*Average height from base (plant grown in hanging basket, so no soil line present) to foliar plane.*—34.0 cm.

*Average height from base (plant grown in hanging basket, so no soil line present) to top of floral plane.*—41.2 cm.

*Plant spread.*—Average of 40.5 cm.

*Appropriate container size.*—8 cm by 2 cm rectangular hanging basket.

*Growth rate.*—Moderate.

*Plant vigor.*—Moderate.

*Propagation type.*—Meristematic tissue culture propagation using the base of the leaves.

*Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility.*—Plants have not been observed to be susceptible or resistant to pathogens and pests common to *Vanda*.

*Environmental tolerances.*—Adapt to, at least, USDA Zones 11 and 12 and temperatures as high as 40 degrees Celsius; high tolerance to rain; moderate to high tolerance to wind.

Root system:

*General.*—Moderately to densely rooting; with aerial roots only.

*Dimensions, mature roots.*—50.3 cm long with a diameter of 0.7 cm, on average.

*Texture.*—Very fleshy; non-fibrous.

*Color.*—Greyed-green, nearest to RHS 192D; root apex is yellow-green, RHS 148A.

Stem:

*Branching habit.*—Monopodial; no lateral branches present.

*Number of primary (main) stems per plant.*—One.

*Number of secondary (lateral) branches per plant.*—None.

*Aspect.*—Circular, formed by the leaf sheaths.

*Length.*—17.8 cm.

*Diameter.*—0.9 cm.

*Internode length.*—0.9 cm.

*Pubescence.*—Glabrous.

*Luster.*—Matte.

*Attitude, main stem.*—Near vertical.

*Strength.*—Very strong.

*Color, juvenile.*—Yellow-green, nearest to RHS 145D.

*Color, mature.*—Yellow-green, nearest to RHS 147D.

*Color at internodes.*—Yellow-green, nearest to RHS 147D.

Foliage:

*Arrangement.*—Distichous.

*Dimensions.*—25.5 cm long, excluding the sheath, and 2.6 cm wide.

*Shape of blade.*—Ligulate.

*Aspect.*—Strongly carinate and slightly curled inward.

*Attitude.*—Moderately curled downward.

*Apex.*—Unequal praemorse.

*Base.*—Sheathing.

*Sheath dimensions.*—3.4 cm long and 1.3 cm wide, on average.

*Sheath color.*—Yellow-green, nearest to RHS 145A.

*Margin.*—Entire.

*Pubescence, texture and luster of adaxial surface.*—Glabrous, smooth, and matte.

*Pubescence, texture and luster of abaxial surface.*—Glabrous, smooth, and matte.

*Color.*—Juvenile foliage, adaxial surface — Yellow-green, nearest to RHS 144A, and becoming green towards the margins and apex, nearest to RHS 137B. Juvenile foliage, abaxial surface — Yellow-green, nearest to in between RHS 144A and 144B, and becoming green towards the margins and apex, nearest to RHS 137B. Mature foliage, adaxial surface —

Green, nearest to RHS NN137A. Mature foliage, abaxial surface — Yellow-green, nearest to RHS 146A.

*Venation.*—Pattern — Parallel. Color, adaxial surface — Green, nearest to RHS 139A. Color, abaxial surface — Green, nearest to a mixture of RHS 143B and 143C.

*Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 8.

*Flowers per plant.*—6 open flowers and 2 flower buds.

*Inflorescence height.*—Approximately 21.4 cm (measured from base of lowest flower to top of upper flower).

*Inflorescence diameter.*—Approximately 22.1 cm.

*Peduncle.*—Dimensions — Approximately 29.7 cm long and 0.7 cm wide. Attitude — Generally at a 30 degree angle to lateral branch axis. Strength — Moderately strong. Texture and luster — Glabrous and matte. Color — Yellow-green, nearest to RHS 144A.

Bud:

*Length.*—Average of 1.4 cm.

*Diameter.*—Average horizontal diameter is 1.6 cm; the vertical diameter is 2.0 cm.

*Shape.*—Cubic, with a deltoid apex which is pointed downward.

*Pubescence, texture and luster.*—Glabrous, smooth and moderately glossy.

*Color.*—Greyed-purple, nearest to RHS 183D, and suffused with a darker shade of purple towards the apex, nearest to a mixture of RHS 183A and 183B; becoming yellow-green towards the base, nearest to a mixture of RHS 145A and 145B.

Flower:

*Flower type.*—Zygomorphic (orchidaceous), typical shape for the genus *Vanda*.

*Flowering habit.*—Moderately free flowering.

*Shape.*—Zygomorphic, single; consisting of three sepals and three petals, one of which is transformed into a labellum; the two lateral petals moderately overlap the lateral and dorsal sepals; lateral sepals slightly to moderately overlap one another.

*Attitude.*—Flowers are outward-facing to slightly nodding.

*Vertical height.*—Approximately 12.2 cm.

*Diameter.*—Approximately 11.3 cm.

*Depth.*—Approximately 5.0 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.7 cm. Width — Approximately 5.5 cm. Shape — Broad ovate. Apex — Obtuse. Base — Cuneate. Margin — Entire; slightly undulated. Pubescence, texture and luster of upper surface — Glabrous, velvety and matte. Pubescence, texture and luster of lower surface — Glabrous, velvety and matte. Color when opening, upper surface — A mixture of purple and white, nearest to RHS 75C and NN155C, and suffused with red-purple towards the margins and apex, nearest to RHS 70B; base of petals is greyed-purple, nearest to RHS 187C; petals are heavily dotted red-purple, nearest to a mixture of RHS 71A, 71B, 71C, and 71D. Color when opening, lower surface — White, nearest to RHS N155A, and suffused with red-purple towards the margins and apex, nearest to RHS 72B; petals with reticulate veining colored purple, nearest to RHS 75A. Color when fully opened, upper surface — A mixture of purple and white, nearest to RHS 75C and 155A, and suffused with red-purple towards the margins and apex, nearest to RHS 64C; base of petals is greyed-purple, nearest to RHS 187B; petals are heavily dotted and veined with a mixture of red-purple and greyed-purple, nearest to RHS 59A, 59B, and 187B. Color when fully opened, lower surface — White, nearest to RHS N155A, and suffused with red-purple towards the margins and apex, nearest to RHS 70A; petals with reticulate veining colored purple, nearest to RHS 75A. Fading, upper surface — Not fading. Fading, lower surface — Not fading. Venation color, fully opened, upper surface — A mixture of red-purple and greyed-purple, nearest to RHS 59A, 59B, and 187B. Venation color, fully opened, lower surface — Purple, nearest to RHS 75A.

*Labellum.*—Shape — Three-lobed; the lateral lobes are obovate and involute; the central lobe is obovate to oblong and strongly revolute. Length — Central lobe — Approximately 2.3 cm. Lateral lobes — Approximately 0.8 cm. Width — Central lobe — Approximately 1.4 cm at the base; 0.9 at the apex. Lateral lobes — Approximately 0.7 cm. Apex — Central lobe — Cleft. Lateral lobes — Obtuse. Base — Central lobe — Broad cuneate. Lateral lobes — Broad cuneate. Margin — Central lobe — Entire; slightly undulated. Lateral lobes — Entire; not undulated. Texture and luster of upper surface — Central lobe — Glabrous, velvety, and slightly glossy. Lateral lobes — Glabrous, velvety, and matte. Texture and luster of lower surface — Central lobe — Glabrous, velvety, and matte except for the apex which is slightly glossy. Lateral lobes — Glabrous, velvety, and matte. Color when opening, upper surface — Central lobe — Nearest to in between red-purple and purple, RHS 59A and RHS N79B and N79C; fading slightly lighter towards the apex, nearest to RHS N79B; becoming red-purple towards the base, nearest to RHS 71B. Lateral lobes — Red-purple, nearest to RHS 60C, and radially striped yellow-white, nearest to RHS 158D; base is suffused with purple, nearest to RHS 75D. Color when opening, lower surface — Central lobe — Red-purple, nearest to RHS 70B, and becoming darker towards the apex, nearest to RHS 71A. Lateral lobes — Red-purple, nearest to in between RHS 70B and 70C, and radially striped yellow-white, nearest to RHS 158D. Color when fully opened, upper surface — Central lobe — Nearest to in between red-purple and purple, RHS 59A and RHS N79B and N79C; fading slightly lighter towards the apex, nearest to in between RHS N79A and N79B; becoming red-purple towards the base, nearest to RHS 71B. Lateral lobes — Red-purple, nearest to RHS 60C, and radially striped yellow-white, nearest to RHS 158D; base is suffused with purple, nearest to RHS 75D. Color when fully opened, lower surface — Central lobe — Red-purple, nearest to RHS 70B, and becoming darker towards the apex, nearest to RHS 71A. Lateral lobes — Red-purple, nearest to in between RHS 70B and 70C, and radially striped yellow-white, nearest to RHS 158D. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities.*—Dimensions — 1.6 cm long and 0.8 cm wide, on average. Color — Nearest to in between red-purple and purple, RHS 59A and RHS N79B and N79; becoming purple towards the base, nearest to RHS 75B.

*Spurs.*—Quantity — Average of 1. Length — Approximately 0.8 cm. Diameter — Approximately 0.3 cm. Vertical height — Approximately 0.8 cm, at the base. Shape — Short triangular; flattened. Apex — Bluntly acute. Base — Broad cuneate. Pubescence, texture and luster — Glabrous, smooth, and matte. Color — Purple, nearest to RHS 75C, and radially striped purple, nearest to RHS N75B.

*Sepals.*—Quantity — Average of 3 unfused sepals. Arrangement — One dorsal sepal and two lateral sepals. Length — Dorsal sepal — Approximately 6.2 cm. Lateral sepals — Approximately 6.3 cm. Width — Dorsal sepal — Approximately 6.3 cm. Lateral sepals — Approximately 7.2 cm. Shape — Dorsal sepal — Broad ovate. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; lightly undulated. Lateral sepals — Entire; lightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — A mixture of purple and white, nearest to RHS 75C and NN155C, and suffused with red-purple towards the margins and apex, nearest to RHS 70B; base of petals is greyed-purple, nearest to RHS 187C; petals are heavily dotted red-purple, nearest to a mixture of RHS 71A, 71B, 71C, and 71D. Lateral sepals — Nearest to in between red-purple and greyed-orange, RHS 69D and N170D, and becoming red-purple towards the margins and apex, nearest to in between RHS 70B and 70C; sepals are heavily dotted and veined greyed-purple towards the base, nearest to a mixture of RHS N186D and 187B. Color when opening, lower surface — Dorsal sepal — White, nearest to RHS N155A, and suffused with red-purple towards the margins and apex, nearest to RHS 72B; sepals with reticulate veining colored purple, nearest to RHS 75A. Lateral sepals — Purple, nearest to a mixture of RHS N75A and N75B, and fading to white towards the base, nearest to RHS N155A; sepals with reticulate veining colored purple, nearest to a mixture of RHS N78B and N78C. Color when fully opened, upper surface — Dorsal sepal — A mixture of purple and white, nearest to RHS 75C and 155A, and suffused with red-purple towards the margins and apex, nearest to RHS 64C; base of petals is greyed-purple, nearest to RHS 187B; petals are heavily dotted and veined with a mixture of red-purple and greyed-purple, RHS 59A, 59B, and 187B. Lateral sepals — Greyed-orange, nearest to in between RHS 164D and N170D, and becoming greyed-purple towards the margins and apex, nearest to RHS 185D; sepals are heavily dotted and veined greyed-purple, nearest to a mixture of RHS N187B and 187C. Color when fully opened, lower surface — Dorsal sepal — White, nearest to RHS N155A, and suffused with red-purple towards the margins and apex, nearest to RHS 70A; sepals with reticulate veining colored purple, nearest to RHS 75A. Lateral sepals, proximal one-half portion — White, nearest to RHS 155B, and suffused with red-purple towards the margins and apex, nearest to RHS 70B; sepals are veined purple, nearest to RHS 77B. Lateral sepals, distal one-half portion — Greyed-orange, nearest to RHS 164D, and suffused with red-purple towards the margins and apex, nearest to RHS 70B; sepals are veined purple, nearest to RHS N77B. Fading, upper surface — Not fading. Fading, lower surface — Not fading. Venation — Densely reticulate. Venation color, fully opened, upper surface — Dorsal sepal — Nearest to a mixture of red-purple and greyed-purple, RHS 59A, 59B and 187B. Lateral sepals — Greyed-purple, nearest to a mixture of RHS 187B and 187C. Venation color, fully opened, lower surface — Dorsal sepal — Purple, nearest to RHS 75A. Lateral sepals, proximal one-half portion — Purple, nearest to RHS 77B. Lateral sepals, distal one-half portion — Purple, nearest to RHS N77B.

*Pedicels.*—Length — Approximately 5.9 cm. Diameter — Approximately 0.6 cm. Attitude — Approximately 80 degree angle to peduncle axis. Strength — Moderately strong. Texture — Glabrous, axially angled with 5 "ribs", axially twisted (due to resupination). Luster — Moderately glossy. Color — Red-purple, nearest to in between RHS 72A and 72B; ribs are purple, nearest to RHS 76D.

*Bract.*—Quantity — One bract present at the base of each pedicel. Shape — Reniform; folded around the base of each pedicel. Dimensions — Average of 1.7 cm long and 1.8 cm wide. Apex — Slightly praemorse. Base — Broad cuneate. Margins — Entire. Color, inner surface — Yellow-green, nearest to RHS N144D. Color, outer surface — Yellow-green, nearest to RHS N144D.

Reproductive organs:

*Column.*—Length — Approximately 0.7 cm. Diameter — Approximately 0.9 cm. Color — Red-purple, nearest to RHS 69B; upper side is suffused with a darker shade of red-purple, nearest to RHS 71C.

*Ovary.*—Position — Inferior. Diameter — Approximately 0.2 cm. Color — Green-white, nearest to RHS 157D.

*Pollinia color.*—Yellow-orange, nearest to RHS 14A.

Seed and fruit: No fruit and seed production has been detected to date.

COMPARISON WITH THE PARENT PLANTS

Plants of the new cultivar 'SPCDW1806' differ from the *Vanda* seed parent, 'M38BP5' (not patented), by the characteristics described in Table 1.

TABLE 1

| Characteristic | 'SPCDW1806' | 'M38BP5' |
|---|---|---|
| Growth habit. | More compact growth. | Less compact growth. |
| Bloom habit. | More freely flowering. | Less freely flowering. |
| Inflorescence height. | Shorter than 'M38BP5'. | Longer than 'SPCDW1806'. |
| Flower size. | Larger than 'M38BP5'. | Smaller than 'SPCDW1806'. |
| Expression of the overlaid color pattern of the petals and sepals. | More conspicuously reticulated. | More subtly reticulated. |

Plants of the new cultivar 'SPCDW1806' differ from the *Vanda* pollen parent, *Vanda* 'M81R1' (not patented), by the characteristics described in Table 2.

TABLE 2

| Characteristic | 'SPCDW1806' | 'M81R1' |
|---|---|---|
| Growth habit. | More compact growth. | Less compact growth. |
| Bloom habit. | More freely flowering. | Less freely flowering. |
| Inflorescence height. | Shorter than 'M81R1'. | Longer than 'SPCDW1806'. |
| Flower size. | Smaller than 'M81R1'. | Larger than 'SPCDW1806'. |
| Expression of the overlaid color pattern of the petals and sepals. | More conspicuously reticulated and spotted. | More subtly spotted and reticulated. |

COMPARISON WITH THE MOST SIMILAR *VANDA* CULTIVAR KNOWN TO THE INVENTOR

Plants of the new cultivar 'SPCDW1806' are similar to the cultivar, *Vanda* 'SPCDW1512' (Community Plant Variety Rights grant number 45556). A comparison of 'SPCDW1806' with *Vanda* 'SPCDW1512' is described in Table 3.

TABLE 3

| Characteristic | 'SPCDW1801' | 'SPCDW1512' |
|---|---|---|
| Lateral petal position, relative to the dorsal sepal. | More overlapping. | Less overlapping. |
| General coloration of the petals and sepals when fully opened. | Darker red-purple. | Lighter red-purple. |
| Expression of the overlaid color pattern of the petals and sepals. | Reticulated and spotted. | Spotted. |

That which is claimed is:

1. A new and distinct variety of *Vanda* plant named 'SPCDW1806', substantially as described and illustrated herein.

* * * * *